US008475359B2

(12) United States Patent
Asada et al.

(10) Patent No.: US 8,475,359 B2
(45) Date of Patent: Jul. 2, 2013

(54) MEDICAL APPARATUS

(75) Inventors: Daisuke Asada, Hachioji (JP); Hitoshi Karasawa, Hachioji (JP); Sho Nakajima, Hachioji (JP); Nobuyoshi Yazawa, Hachioji (JP); Tsutomu Urakawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 915 days.

(21) Appl. No.: 12/563,404

(22) Filed: Sep. 21, 2009

(65) Prior Publication Data

US 2010/0076259 A1 Mar. 25, 2010

(30) Foreign Application Priority Data

Sep. 19, 2008 (JP) ................................. 2008-241401

(51) Int. Cl.
*A61B 1/00* (2006.01)
*A61B 1/06* (2006.01)

(52) U.S. Cl.
USPC .......................................... 600/102; 600/173

(58) Field of Classification Search
CPC ............................................ A61B 2017/00283
USPC .......................................... 600/173, 168, 102
See application file for complete search history.

(56) References Cited

U.S. PATENT DOCUMENTS

| | | | | |
|---|---|---|---|---|
| 4,921,393 A * | 5/1990 | Andeen et al. | ................. | 414/729 |
| 5,707,344 A * | 1/1998 | Nakazawa et al. | ............ | 600/127 |
| 5,797,835 A * | 8/1998 | Green | ........................... | 600/106 |
| 6,648,816 B2 * | 11/2003 | Irion et al. | ..................... | 600/173 |
| 7,066,879 B2 | 6/2006 | Fowler et al. | | |
| 7,339,341 B2 * | 3/2008 | Oleynikov et al. | ....... | 318/568.12 |
| 7,841,980 B2 * | 11/2010 | Minosawa et al. | ............ | 600/118 |
| 2002/0165589 A1 * | 11/2002 | Imran et al. | ..................... | 607/40 |
| 2004/0193016 A1 * | 9/2004 | Root et al. | ..................... | 600/146 |
| 2005/0165272 A1 * | 7/2005 | Okada et al. | .................. | 600/114 |
| 2009/0005636 A1 * | 1/2009 | Pang et al. | ..................... | 600/102 |
| 2009/0062604 A1 * | 3/2009 | Minosawa et al. | ............ | 600/104 |
| 2010/0152539 A1 * | 6/2010 | Ghabrial et al. | .............. | 600/118 |

FOREIGN PATENT DOCUMENTS

| | | |
|---|---|---|
| JP | 05-344951 | 12/1993 |
| JP | 2002-204773 | 7/2002 |
| JP | 2004-305525 | 11/2004 |
| WO | WO 2007/056627 A1 | 5/2007 |
| WO | WO 2007/097034 A1 | 8/2007 |
| WO | WO 2007/138567 A2 | 12/2007 |

* cited by examiner

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

A medical apparatus according to the present invention is a medical apparatus used in a state in which the medical apparatus is led into a body and fixed. The medical apparatus includes: a fixing section that fixes the medical apparatus on a body wall in the body; an image pickup section that picks up an image of a subject in the body and is provided pivotably around a first axis; and a holding section that includes the fixing section and holds the image pickup section pivotably around a second axis different from the first axis. Therefore, the medical apparatus can change a photographing range and a visual field direction as desired to photograph the subject by performing magnified observation and photographing the subject from different directions without using a zoom function in the state in which the medical apparatus is fixed in a limited space in the body.

7 Claims, 17 Drawing Sheets

MEDICAL APPARATUS

This application claims benefit of Japanese Application No. 2008-241401 field in Japan on Sep. 19, 2008 the contents of which are incorporated by this reference.

BACKGROUND OF THE INVENTION

1. Field of the Invention

The present invention relates to a medical apparatus including image pickup means that is fixed in a body and used.

2. Description of the Related Art

As is well known, an endoscope as a medical instrument includes an image pickup apparatus. The endoscope is led into a body cavity of a patient and used for performing various inspections, various kinds of treatments, and the like for an affected area in the body using observation images photographed by the image pickup apparatus.

Examples of such an endoscope include an endoscope that is led into digestive organs such as the esophagus, the stomach, the large intestine, and the duodenum, which are luminal tracts in the body, from the anus or the mouth cavity and an endoscope that is led into the abdominal cavity penetrating through the body wall from the vicinity of the navel. In general, the endoscope has a long insertion portion. The insertion portion is inserted into the digestive organ tract or into the abdominal cavity.

As an apparatus that observes the inside of the body in this way, for example, a television camera for intra-body cavity observation disclosed in Japanese Patent Application Laid-Open Publication No. 2002-204773 is proposed. Japanese Patent Application Laid-Open Publication No. 2002-204773 discloses a technique for, such that a visual field direction of the television camera, coupling the other ends of two operation wires wound around a pulley of a first operation knob to two arm pieces of a cross arm, respectively, coupling the other ends of two operation wires wound around a pulley of a second operation knob to the remaining arm pieces, and pivoting a housing, in which image pickup means and illuminating means are mounted, in an arbitrary direction according to the operation of the operation knobs to change a visual field direction of the image pickup means to an arbitrary direction.

For example, Japanese Patent Application Laid-Open Publication No. 2004-305525 discloses an image pickup apparatus that can change a visual field direction thereof. The image pickup apparatus disclosed in Japanese Patent Application Laid-Open Publication No. 2004-305525 includes a spherical housing formed in a spherical shape, image pickup means housed in the spherical housing, a tubular main body, and holding means that is provided in the main body, causes an image pickup visual field section of the image pickup means housed in the spherical housing to project from one end side thereof, pivotably holds the spherical housing, and pivots the entire spherical housing in an arbitrary direction to change a visual field direction of the image pickup means.

For example, Japanese Patent Application Laid-Open Publication No. 5-344951 discloses an abdominal cavity lifting apparatus with endoscope that is space-saving and can reduce damage to a subcutaneous tissue and stereoscopically observe the inside of the abdominal cavity in a laparoscopic surgery. The abdominal cavity lifting apparatus with endoscope disclosed in Japanese Patent Application Laid-Open Publication No. 5-344951 includes plural abdominal wall supporting members that bend and extend from a distal end portion of a column section with respect to a longitudinal direction of the column section. In at least one movable abdominal wall supporting member of the plural abdominal wall supporting members, an image pickup section and a light projecting unit are attached to the column section pivotably around the axis of the column section with the distal end of the column section as a fulcrum and provided in a position a predetermined distance apart from the column section in an extending direction on a surface on which the movable abdominal wall supporting member faces the inside of the body.

SUMMARY OF THE INVENTION

A medical apparatus according to the present invention is a medical apparatus used in a state in which the medical apparatus is led into a body and fixed. The medical apparatus includes: a fixing section that fixes the medical apparatus on a body wall in the body; an image pickup section that picks up an image of a subject in the body and is provided pivotably around a first axis; and a holding section that includes the fixing section and holds the image pickup section pivotably around a second axis different from the first axis. Therefore, the medical apparatus can change a photographing range and a visual field direction as desired to photograph the subject by performing magnified observation and photographing the subject from different directions without using a zoom function in the state in which the medical apparatus is fixed in a limited space in the body.

The above and other objects, features and advantages of the invention will become more clearly understood from the following description referring to the accompanying drawings.

DETAILED DESCRIPTION OF THE PREFERRED EMBODIMENTS

An embodiment of the present invention is explained below with reference to the accompanying drawings. In the following explanation, for example, a medical apparatus for performing a laparoscopic surgical operation is illustrated.

Figure 1:
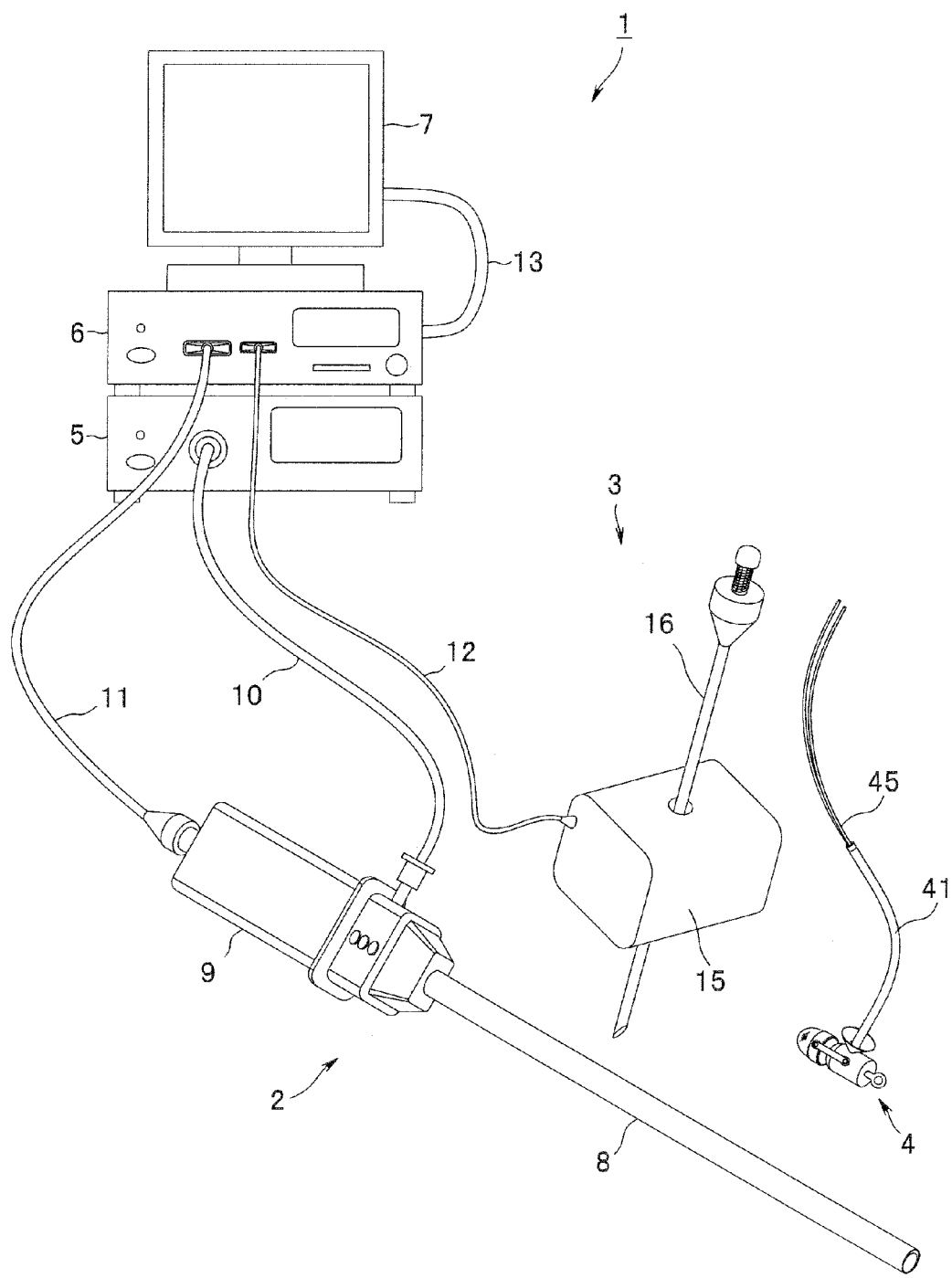
FIG. 1 is a diagram of a configuration of an endoscope system as a medical apparatus according to an embodiment of the present invention.
Figure 2:
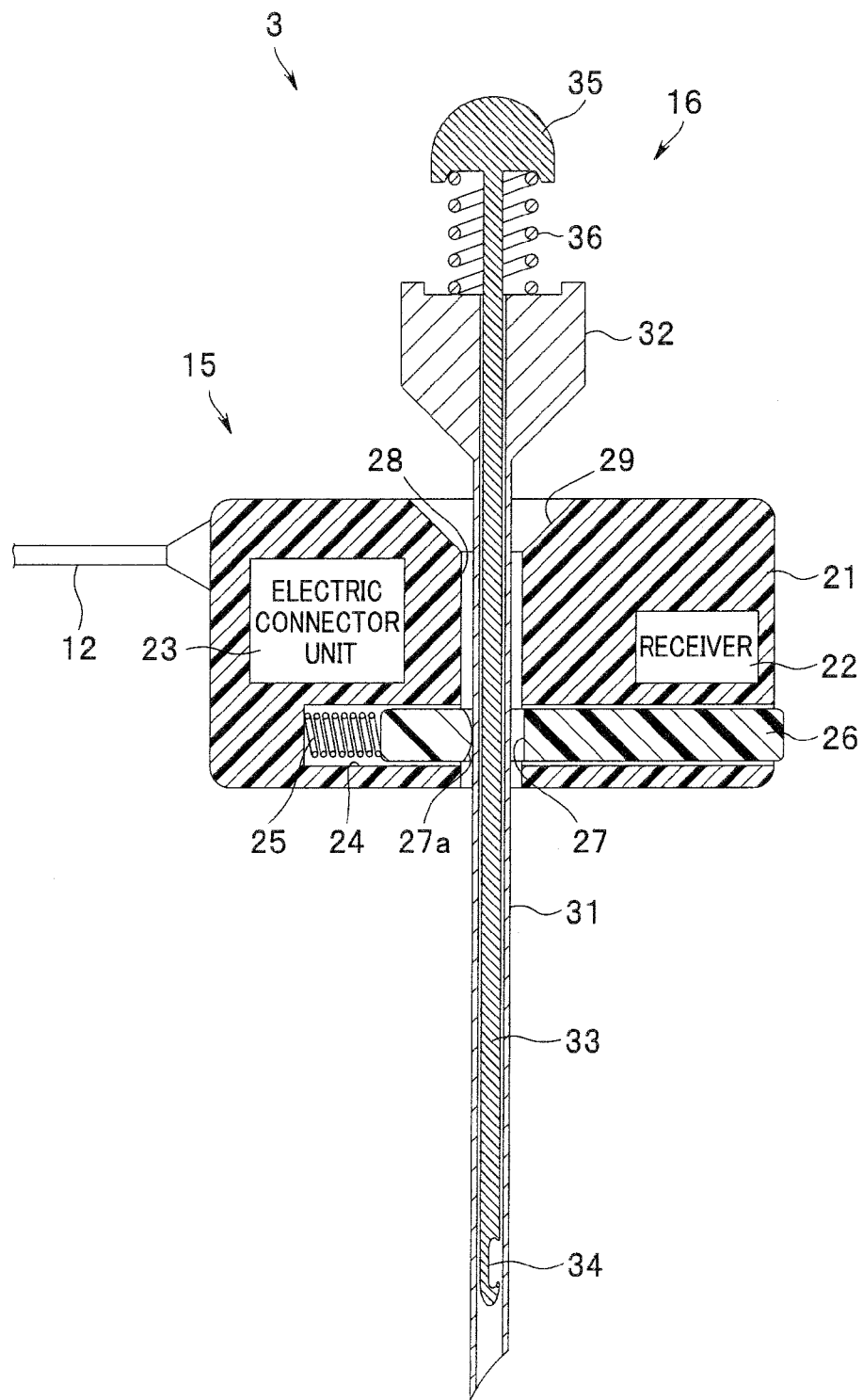
FIG. 2 is a sectional view of a configuration of an external device according to the embodiment.
Figure 3:
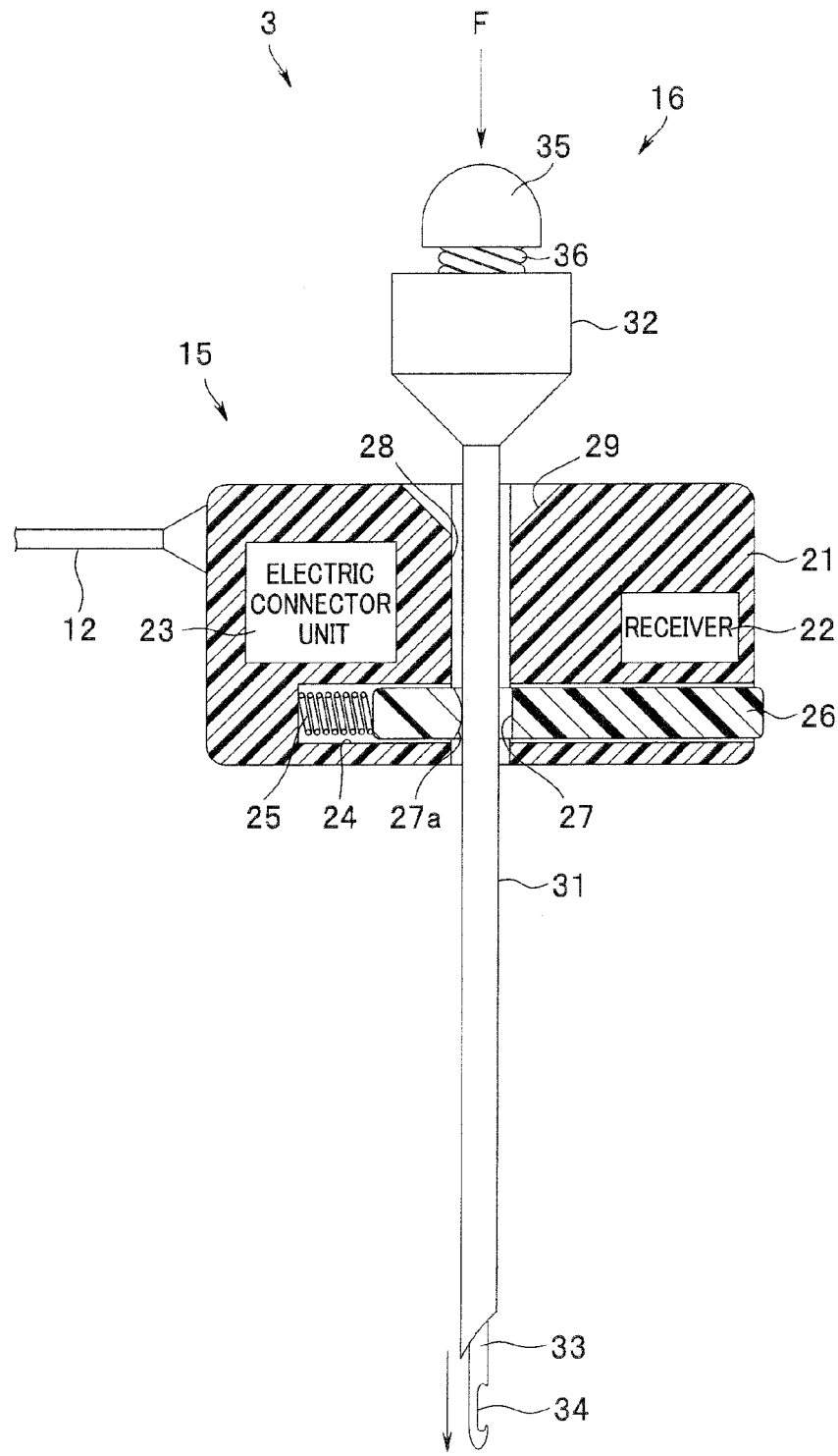
FIG. 3 is a sectional view of an action of a hook needle of the external device according to the embodiment.
Figure 4:
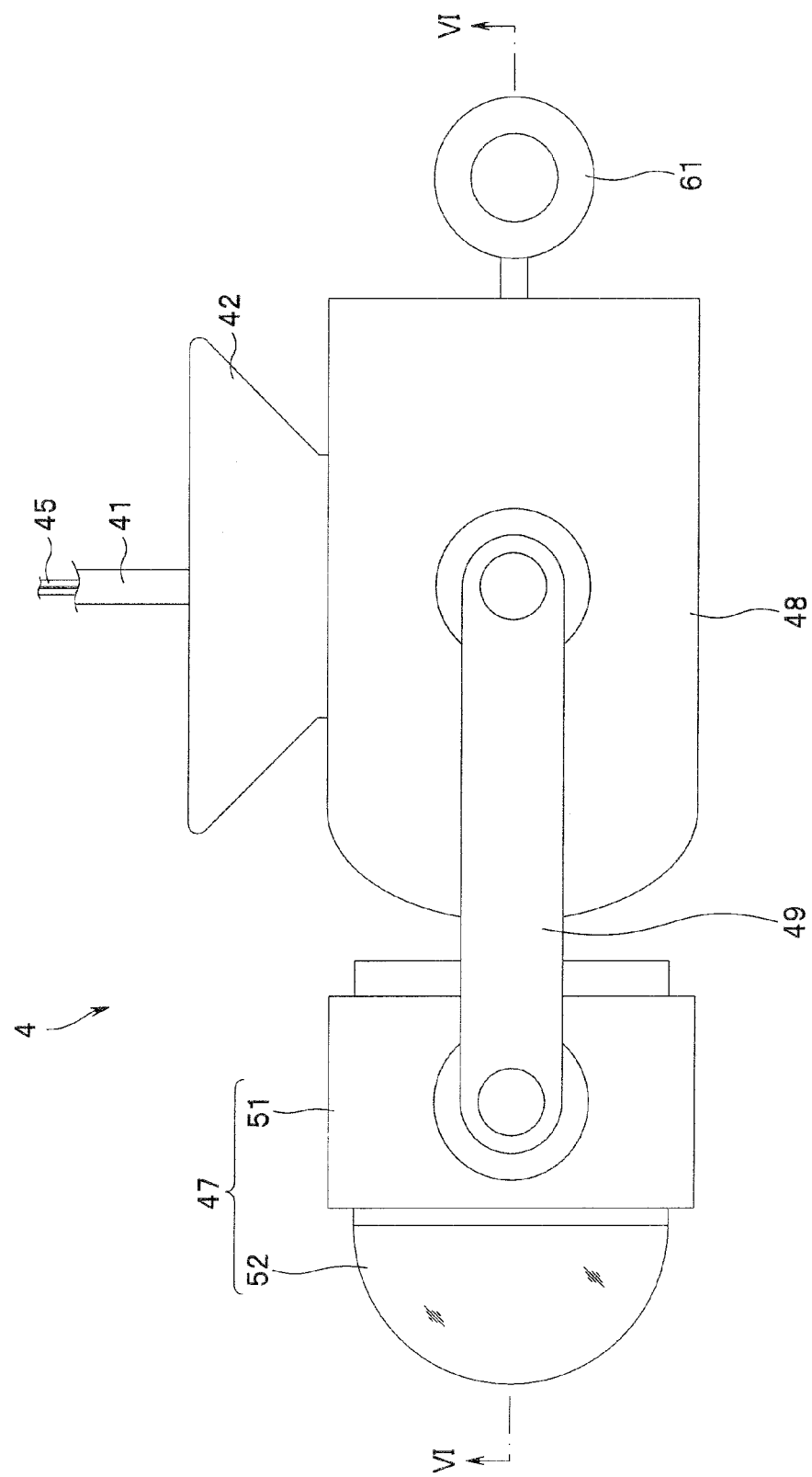
FIG. 4 is a diagram of a configuration of an intra-abdominal cavity set camera according to the embodiment.
Figure 5:
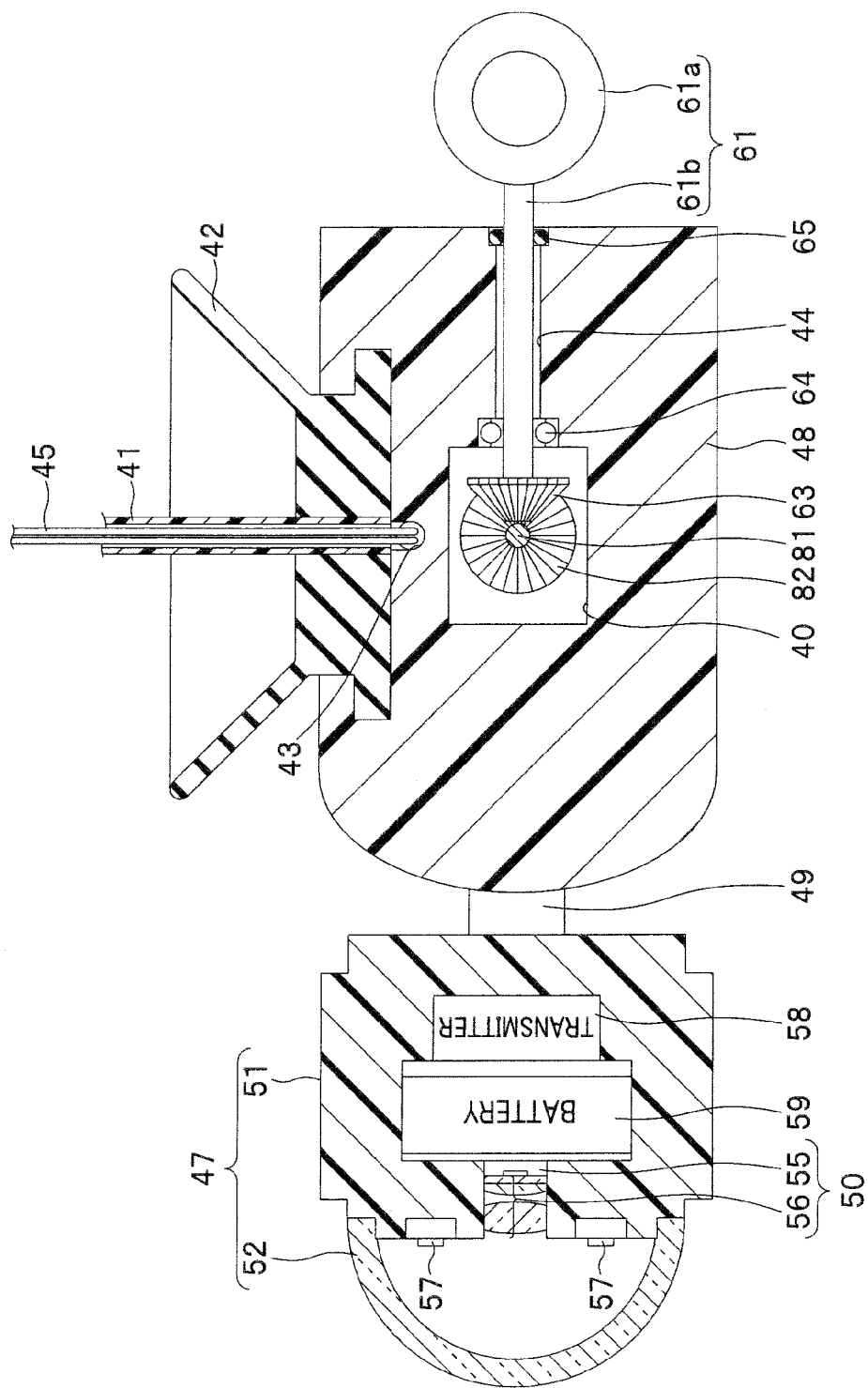
FIG. 5 is a sectional view of the configuration of the intra-abdominal cavity set camera shown in FIG. 4 according to the embodiment.
Figure 6:
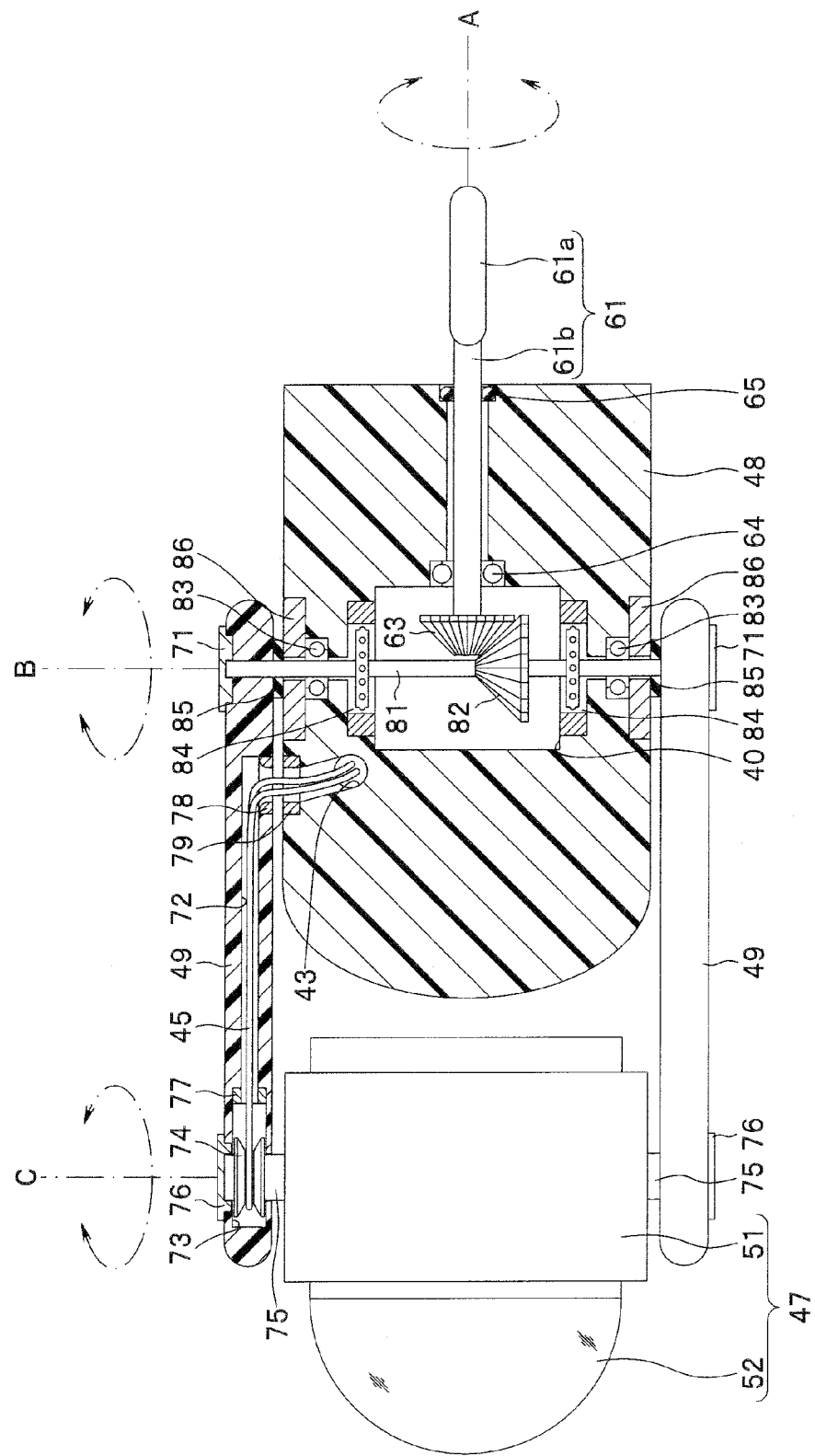
FIG. 6 is a sectional view of the configuration of the intra-abdominal cavity set camera taken along line VI-VI of FIG. 4 according to the embodiment.
Figure 7:
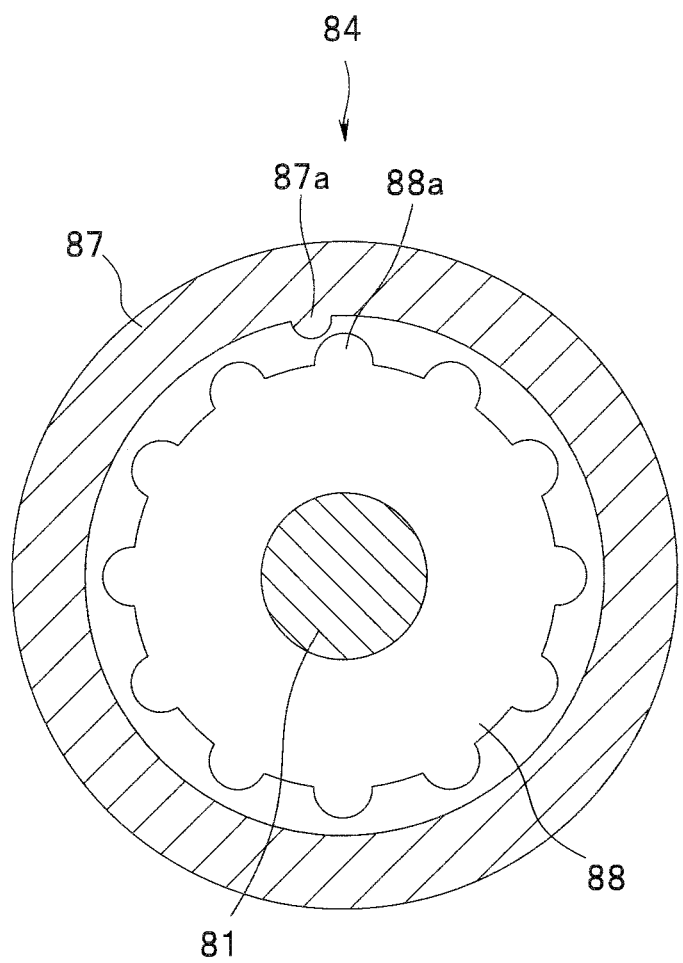
FIG. 7 is a sectional view of a configuration of a click mechanism unit according to the embodiment.
Figure 8:
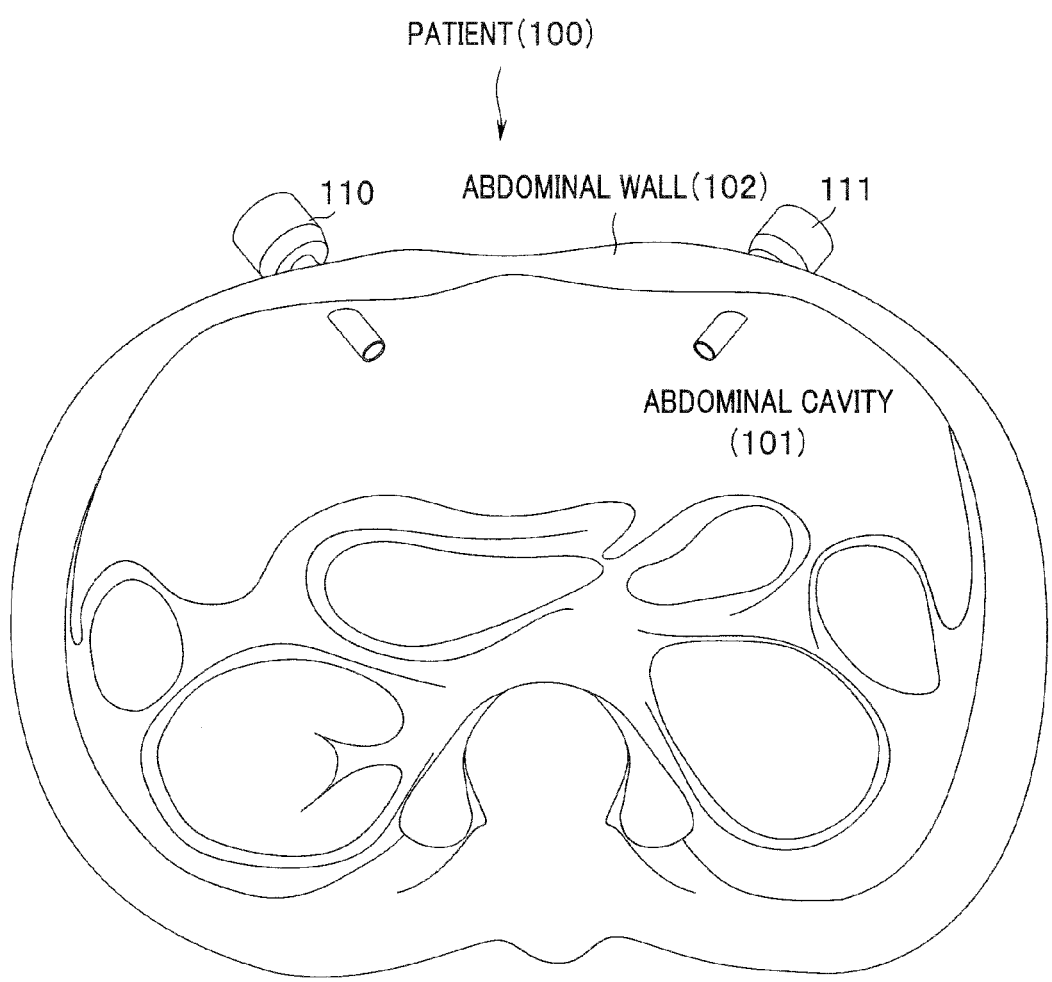
FIG. 8 is a diagram of a state in which a trocar is penetrated through the abdominal wall of a patient according to the embodiment.
Figure 9:
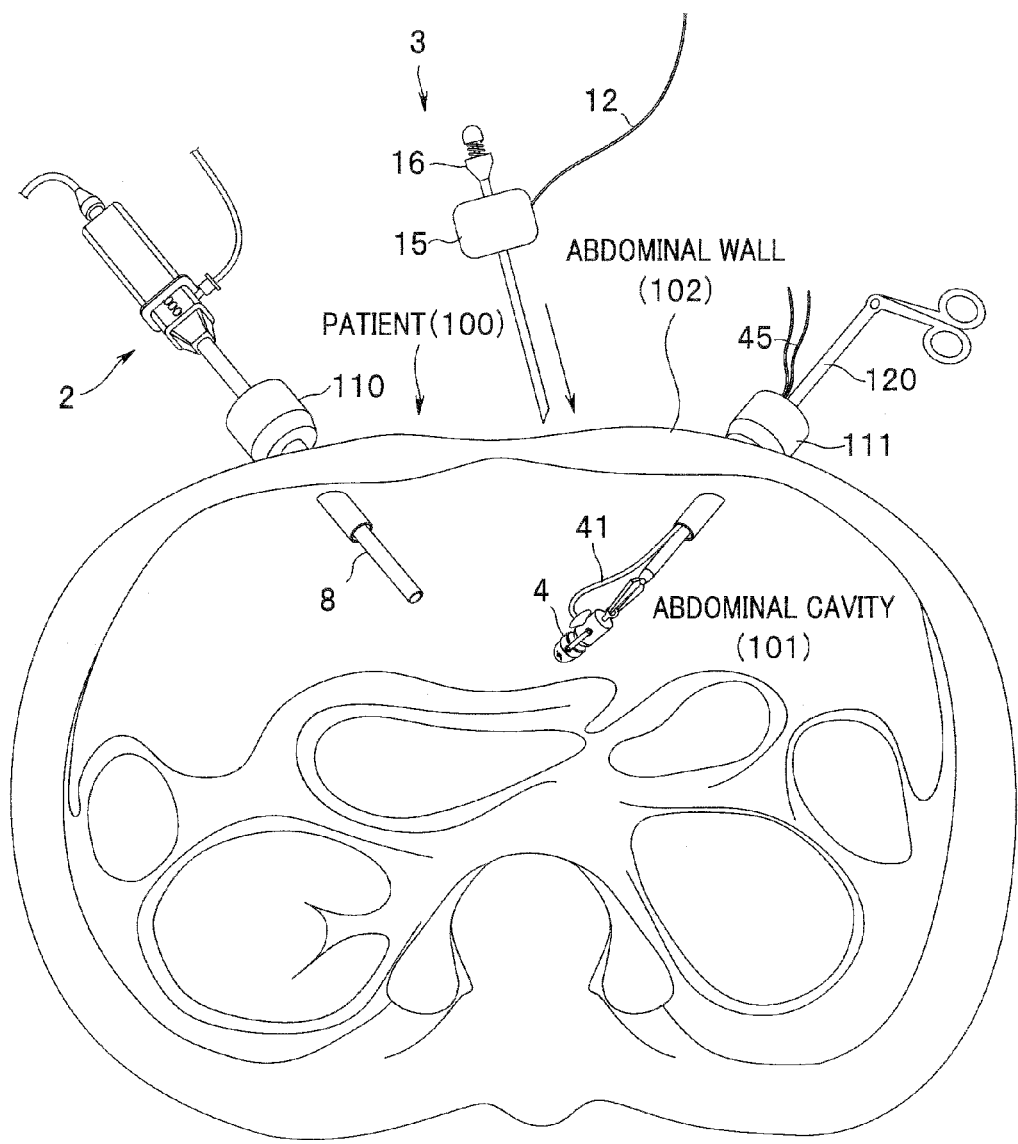
FIG. 9 is a diagram for explaining a procedure for leading the intra-abdominal cavity set camera into the abdominal cavity according to the embodiment.
Figure 10:
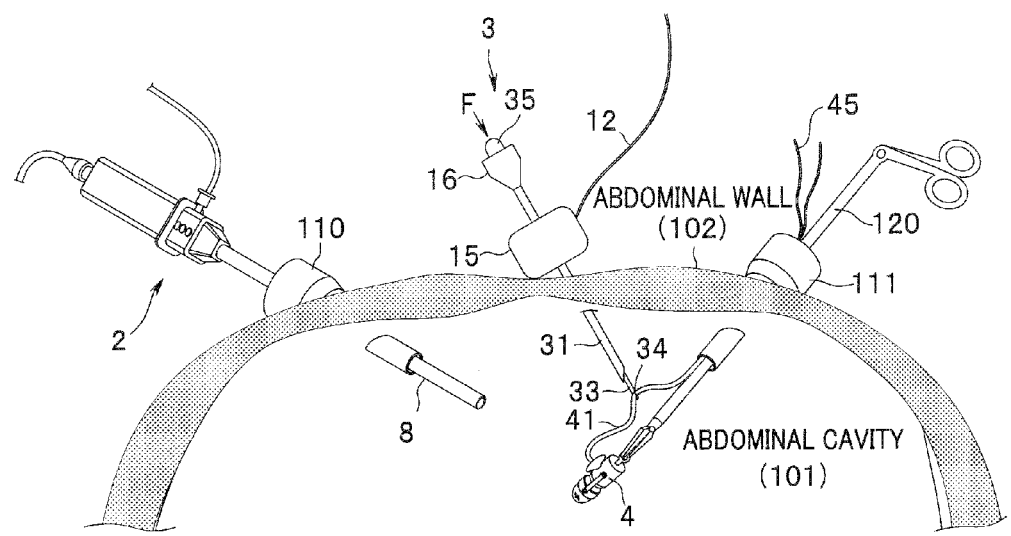
FIG. 10 is a diagram of a state in which the hook needle is penetrated through the abdominal wall to hook a tube member of the intra-abdominal cavity set camera and for explaining a procedure for leading the intra-abdominal cavity set camera into the abdominal cavity according to the embodiment.
Figure 11:
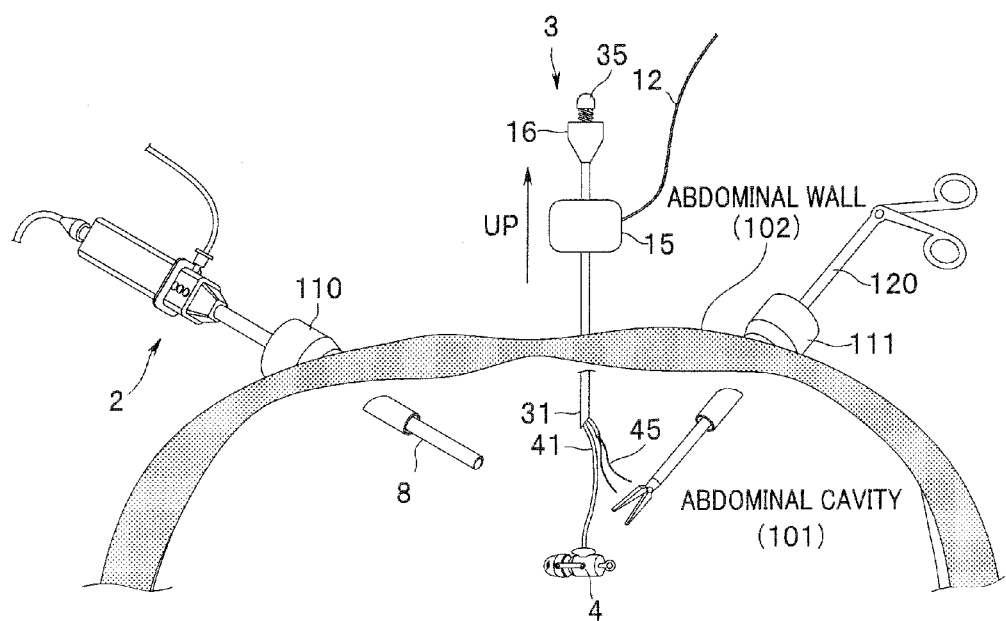
FIG. 11 is a diagram of a state in which the hook needle that hooks the tube member of the intra-abdominal cavity set camera is pulled up and for explaining a procedure for fixing the intra-abdominal cavity set camera to the abdominal wall according to the embodiment.
Figure 12:
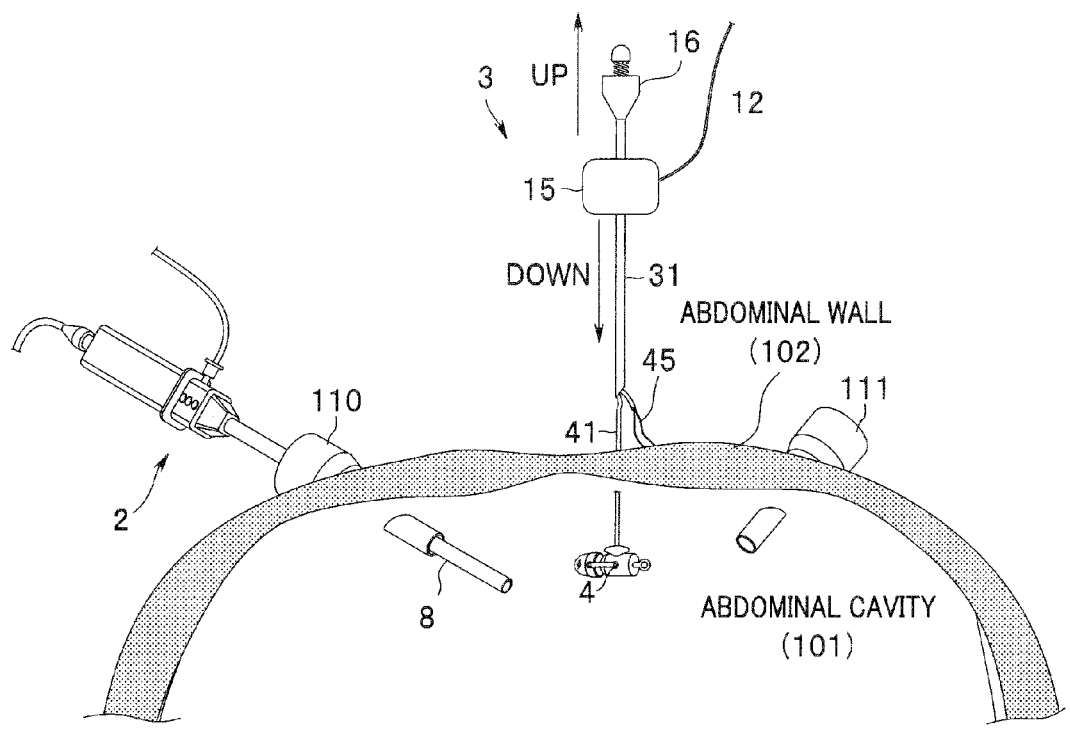
FIG. 12 is a diagram of a state in which the hook needle is pulled up and a fixing unit is lowered along the hook needle and for explaining a procedure for fixing the intra-abdominal cavity set camera to the abdominal wall according to the embodiment.
Figure 13:
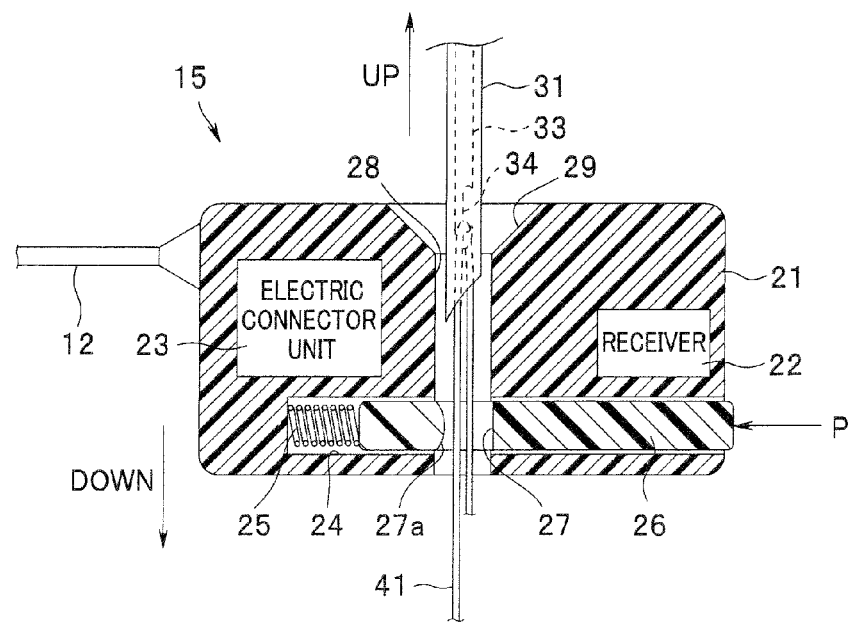
FIG. 13 is a sectional view for explaining an action of the external device according to the embodiment.
Figure 14:
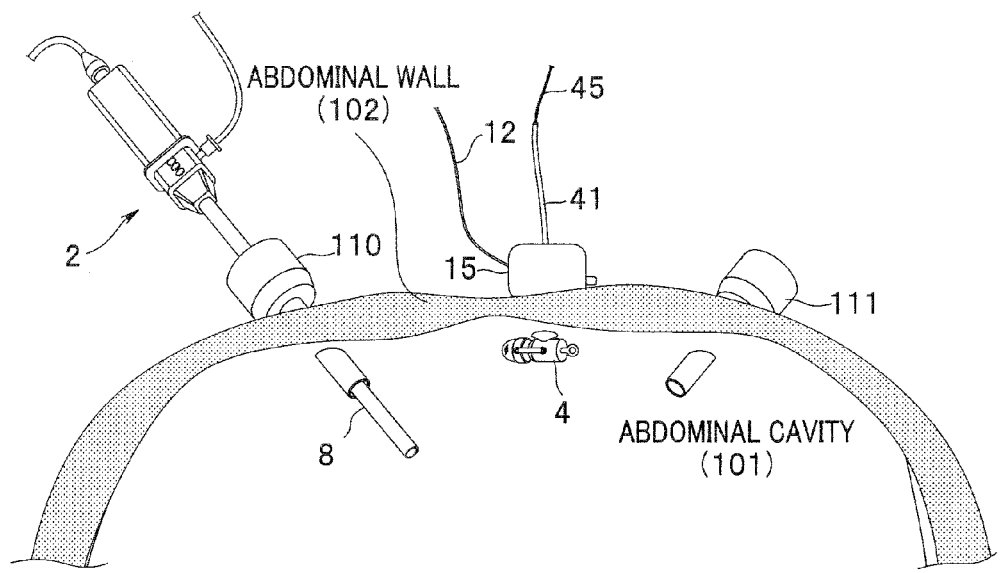
FIG. 14 is a diagram of a state in which the fixing unit is set on the abdomen and the intra-abdominal cavity set camera is fixed to the abdominal wall according to the embodiment.
Figure 15:
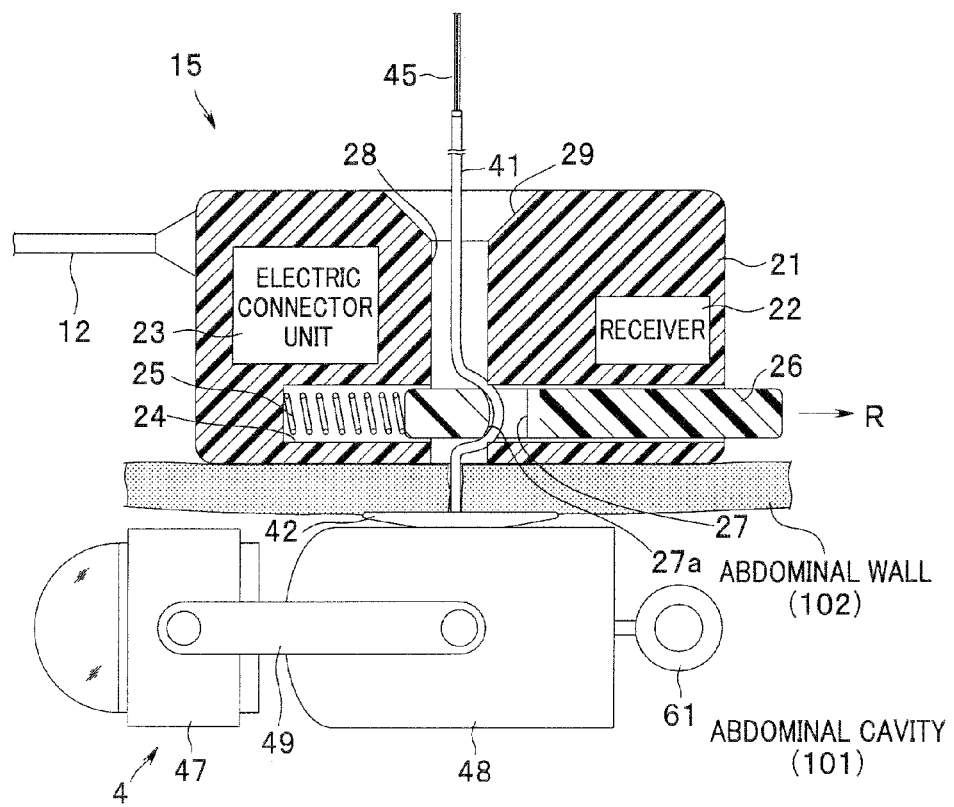
FIG. 15 is a sectional view of the fixing unit and the intra-abdominal cavity set camera in the state shown in FIG. 14 according to the embodiment.
Figure 16:
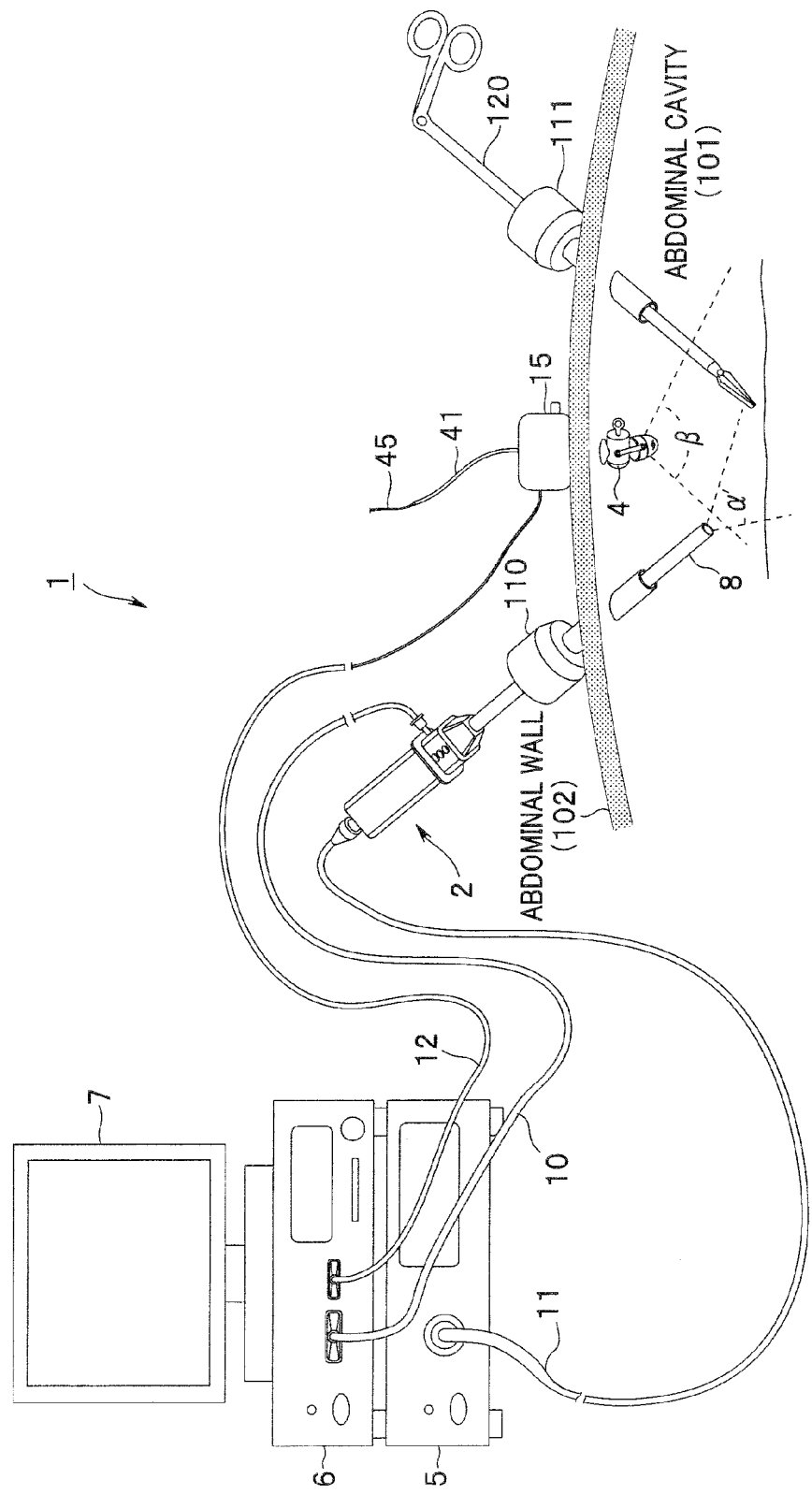
FIG. 16 is an overall diagram of the endoscope system in a state in which the intra-abdominal cavity set camera is fixed to the abdominal wall according to the embodiment.
Figure 17:
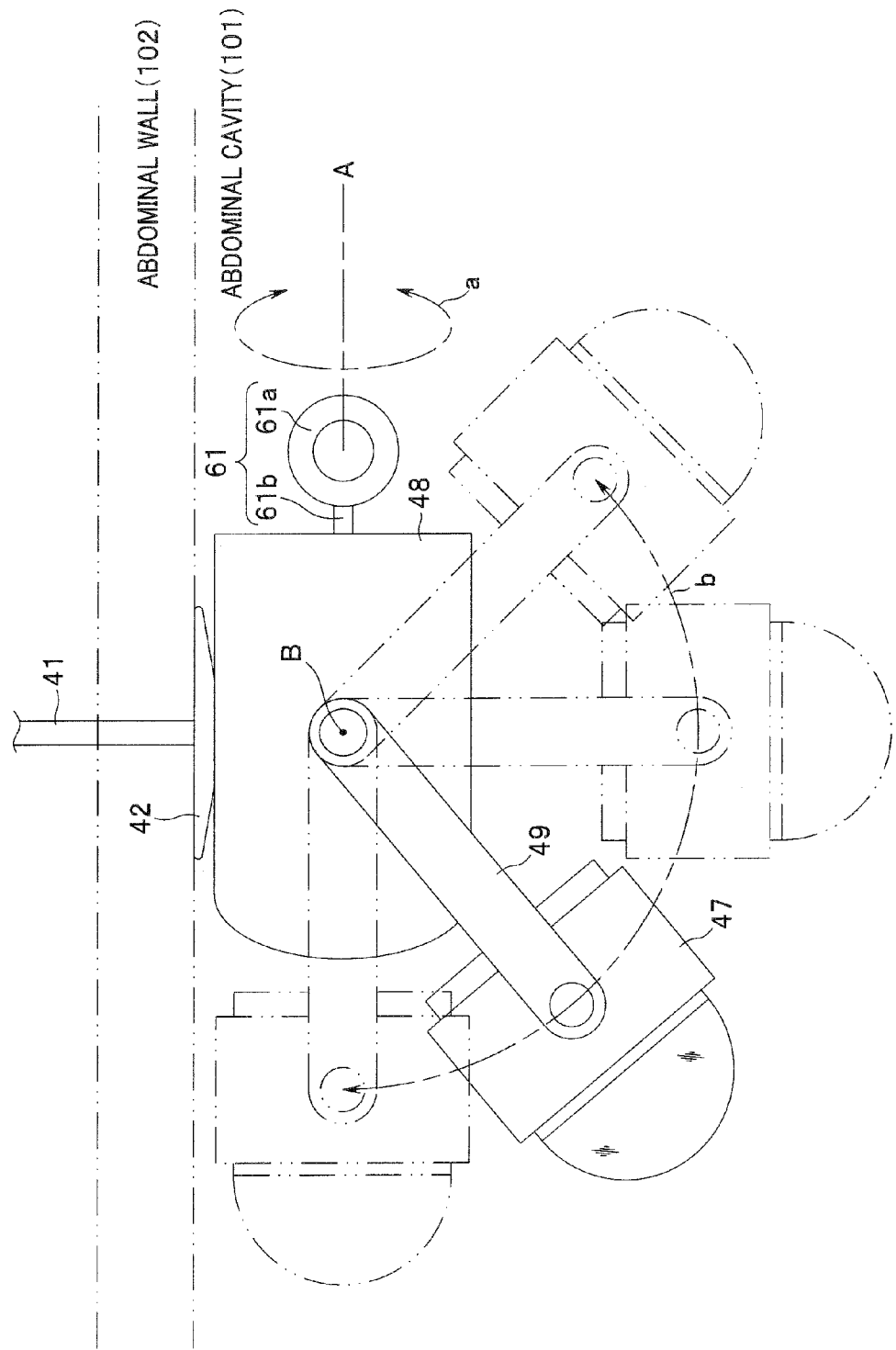
FIG. 17 is a diagram for explaining an action for changing a position of a camera unit of the intra-abdominal cavity set camera with the operation of an operation grasping member according to the embodiment.
Figure 18:
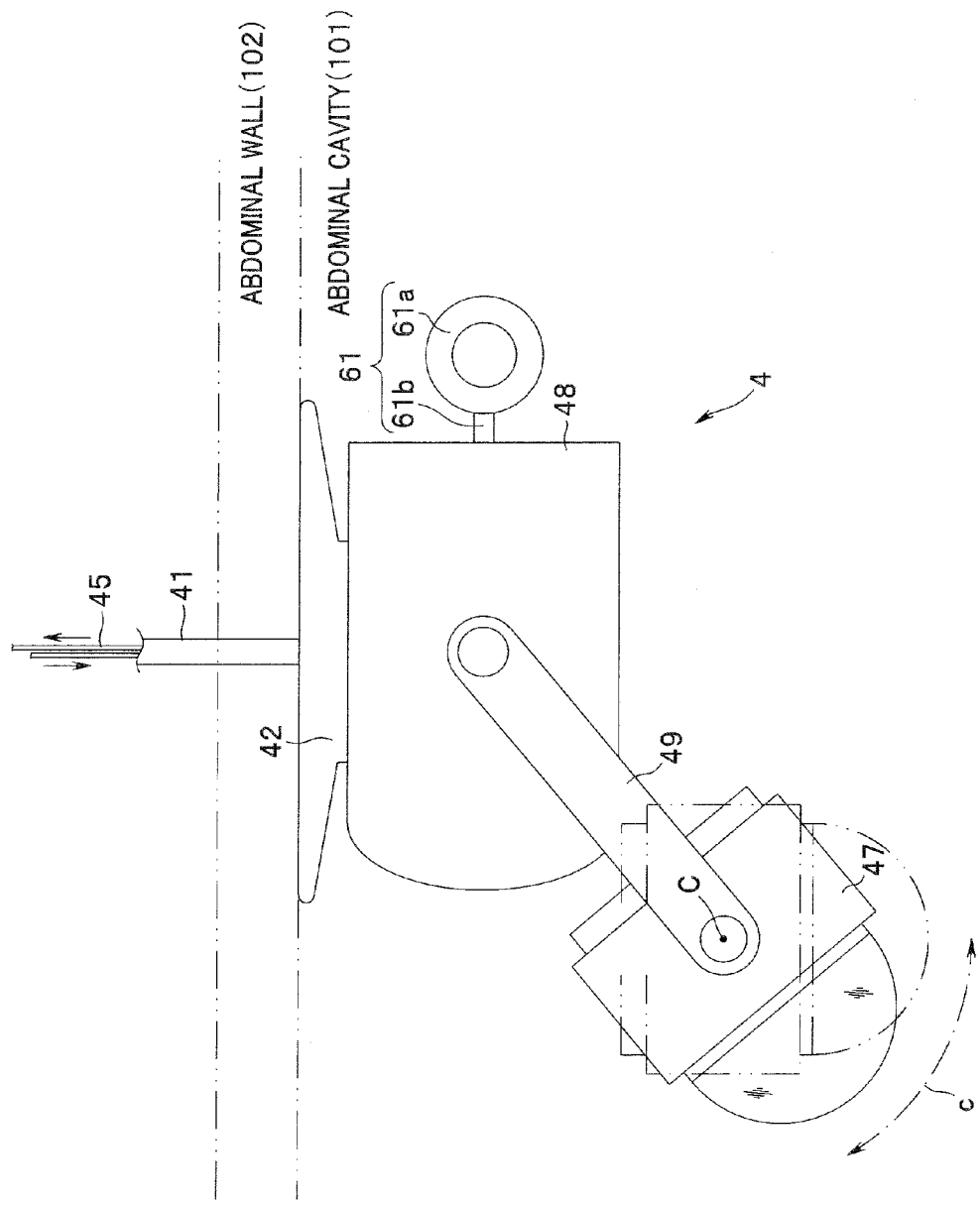
FIG. 18 is a diagram for explaining an action for changing a photographing direction of the camera unit of the intra-abdominal cavity set camera with the operation of an operation wire according to the embodiment.
Figure 19:
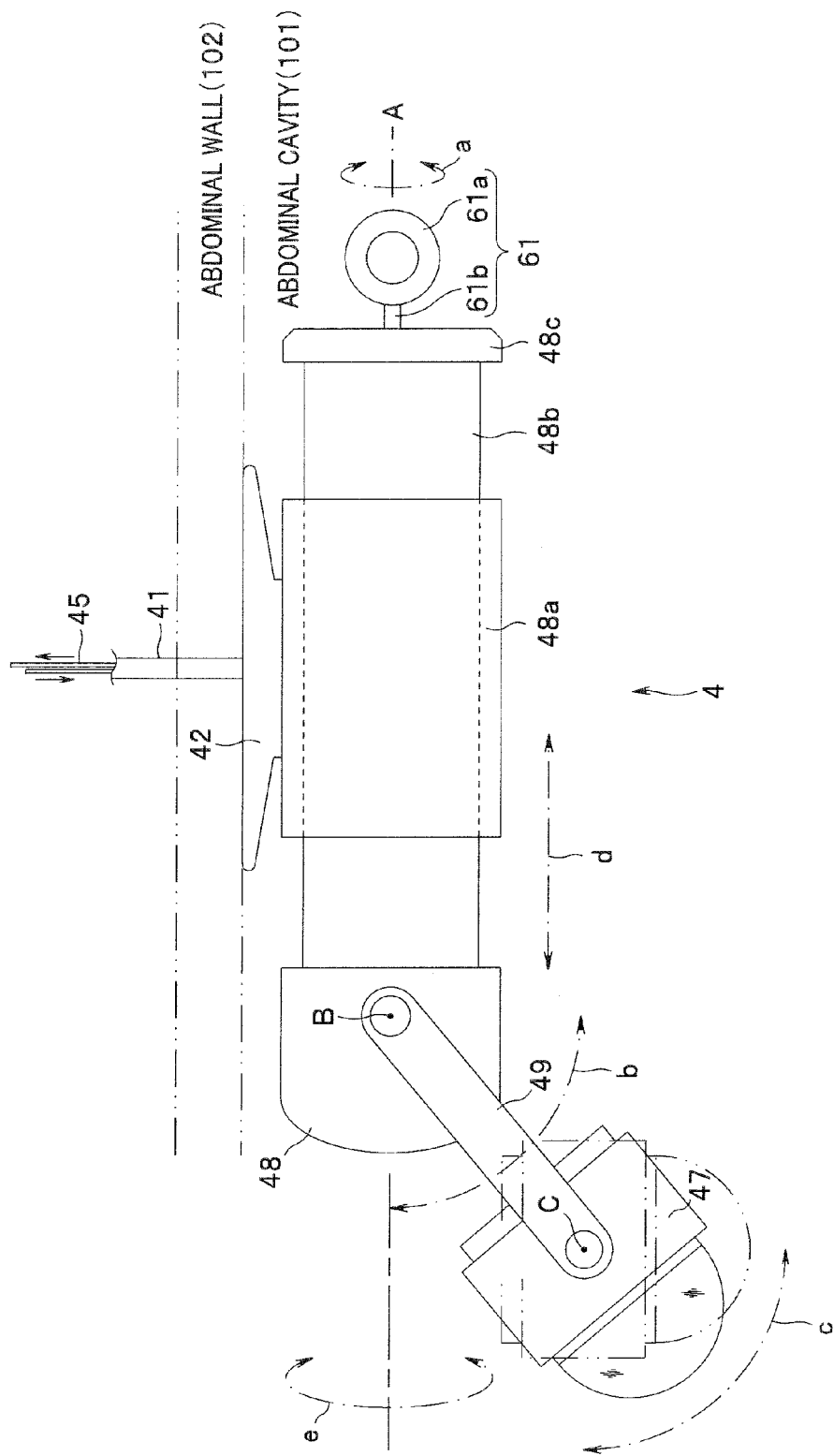
FIG. 19 is a diagram of a configuration of an intra-abdominal cavity set camera according to a first modification of the embodiment.
Figure 20:
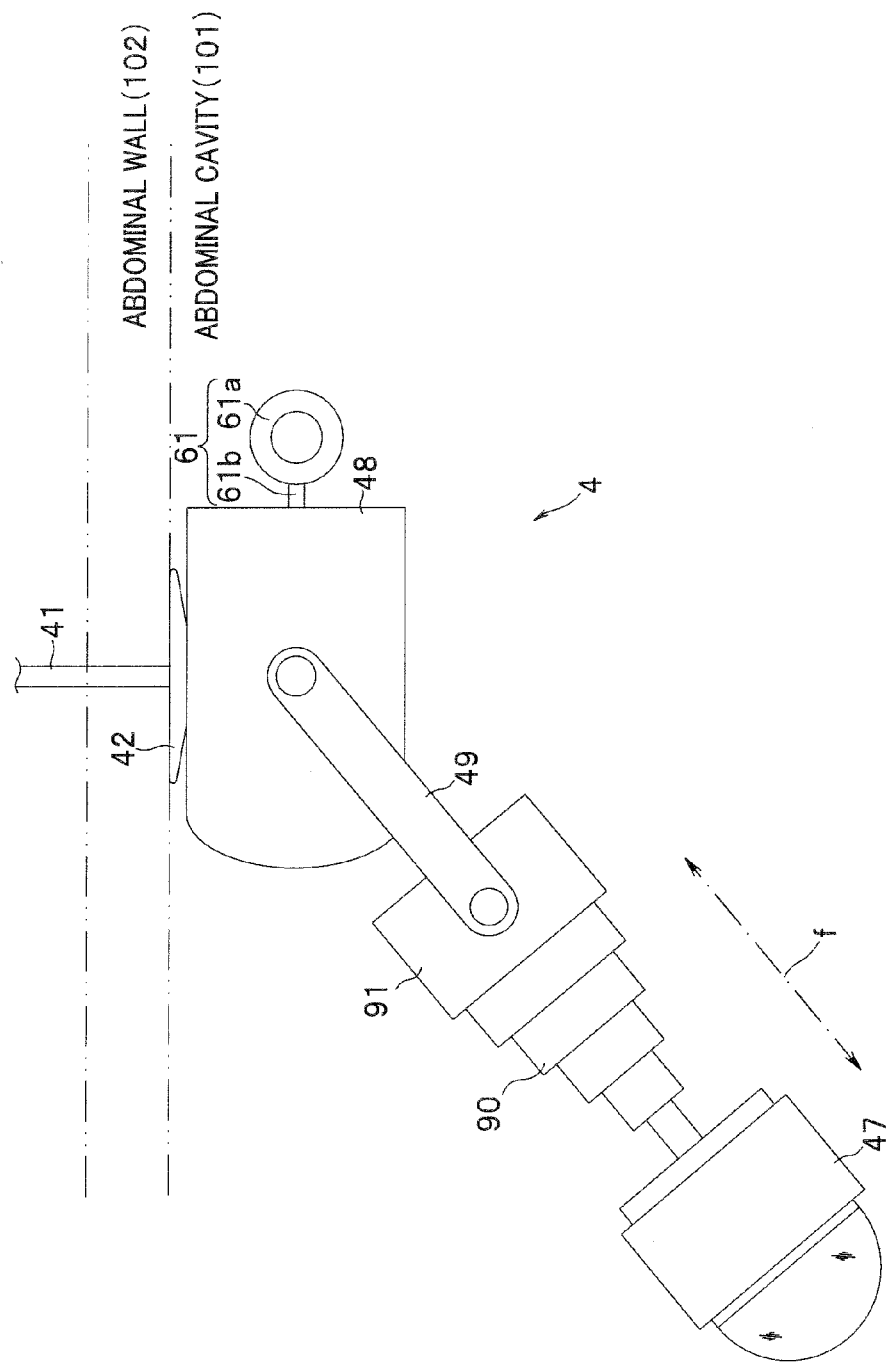
FIG. 20 is a diagram of a configuration of an intra-abdominal cavity set camera according to a second modification of the embodiment.

First, an endoscope system as a medical apparatus according to the present invention used in the laparoscopic surgical operation is explained below. FIGS. 1 to 20 relates to a first embodiment of the present invention. FIG. 1 is a diagram of a configuration of an endoscope system as a medical apparatus. FIG. 2 is a sectional view of a configuration of an external device. FIG. 3 is a sectional view of an action of a hook needle of the external device. FIG. 4 is a diagram of a configuration of an intra-abdominal cavity set camera. FIG. 5 is a sectional view of the configuration of the intra-abdominal cavity set camera shown in FIG. 4. FIG. 6 is a sectional view of the configuration of the intra-abdominal cavity set camera taken along line VI-VI of FIG. 4. FIG. 7 is a sectional view of a configuration of a click mechanism unit. FIG. 8 is a diagram of a state in which a trocar is penetrated through the abdominal wall of a patient. FIG. 9 is a diagram for explaining a procedure for leading the intra-abdominal cavity set camera into the abdominal cavity. FIG. 10 is a diagram of a state in which the hook needle is penetrated through the abdominal wall to hook a tube member of the intra-abdominal cavity set camera and for explaining a procedure for leading the intra-abdominal cavity set camera into the abdominal cavity. FIG. 11 is a diagram of a state in which the hook needle that hooks the tube member of the intra-abdominal cavity set camera is pulled up and for explaining a procedure for fixing the intra-abdominal cavity set camera to the abdominal wall. FIG. 12 is a diagram of a state in which the hook needle is pulled up and a fixing unit is lowered along the hook needle and for explaining a procedure for fixing the intra-abdominal cavity set camera to the abdominal wall. FIG. 13 is a sectional view for explaining an action of the external device. FIG. 14 is a diagram of a state in which the fixing unit is set on the abdomen and the intra-abdominal cavity set camera is fixed to the abdominal wall. FIG. 15 is a sectional view of the fixing unit and the intra-abdominal cavity set camera in the state shown in FIG. 14. FIG. 16 is an overall diagram of the endoscope system in a state in which the intra-abdominal cavity set camera is fixed to the abdominal wall. FIG. 17 is a diagram for explaining an action for changing a position of a camera unit of the intra-abdominal cavity set camera with the operation of an operation grasping member. FIG. 18 is a diagram for explaining an action for changing a photographing direction of the camera unit of the intra-abdominal cavity set camera with the operation of an operation wire. FIG. 19 is a diagram of a configuration of an intra-abdominal cavity set camera according to a first modification. FIG. 20 is a diagram of a configuration of an intra-abdominal cavity set camera according to a second modification.

As shown in FIG. 1, an endoscope system 1 according to the present embodiment that performs the laparoscopic surgical operation mainly includes a rigid endoscope 2 as a first photographing device, an external device 3, an intra-abdominal cavity set camera (hereinafter abbreviated as camera) 4, which is an extremely small medical apparatus, as a second photographing device and an image pickup apparatus including image pickup means as an image pickup section, a light source device 5, a camera control unit (hereinafter abbreviated as CCU) 6 as a signal processing device incorporating an image processing circuit, and a display device 7 that is connected to the CCU 6 by a communication cable 13 and displays an observation image.

The light source device 5 supplies illumination light to an illumination optical system included in the rigid endoscope 2. The light source device 5 and the rigid endoscope 2 are detachably connected by a light source cable 10.

The rigid endoscope 2 mainly includes a rigid insertion portion 8 and an operation portion 9 connected to a proximal end portion of the insertion portion 8. An image guide and a light guide bundle are inserted through the insertion portion 8 of the rigid endoscope 2. A photographing optical system that condenses light of a subject image on a camera for rigid endoscope explained later via the image guide and an illumination optical system that irradiates illumination light from the light guide bundle to the subject are disposed on a distal end surface of the insertion portion 8.

A not-shown camera head in which a solid-state image pickup device such as a CCD or a CMOS is arranged is incorporated in the operation portion 9 of the rigid endoscope 2. An optical image of an observed region illuminated by the illumination light supplied from the light source device 5 to the rigid endoscope 2 via the light source cable 10 is picked up by the camera head in the operation portion 9 via the image guide of the insertion portion 8. The camera for rigid endoscope photoelectrically converts the picked-up optical image into an image pickup signal. The image pickup signal is transmitted to the CCU 6 via an image pickup cable 11. An image pickup optical system is set in the rigid endoscope 2 according to the present embodiment such that a photographable angle of view a thereof (see FIG. 16) is, for example, 70° to 75°.

The CCU 6 generates a video signal based on the transmitted image signal and outputs the video signal to the display device 7. The display device 7 is, for example, a liquid crystal display. The display device 7 receives the video signal outputted from the CCU 6 and displays a normal observation image formed by the rigid endoscope 2 and a wide angle observation image formed by the camera 4 on a screen as multi-two-screen display or individually displays the images in a switching manner. The CCU 6 is detachably connected to a fixing unit 15 of the external device 3 explained later by an electric cable 12.

The external device 3 is explained in detail with reference to FIGS. 2 and 3.

As shown in FIGS. 2 and 3, the external device 3 includes the fixing unit 15 that tugs and fixes the camera 4 in the body cavity and a hook needle 16 as a puncture needle that hooks and pulls up the camera 4.

In the fixing unit 15, a receiver 22 and an electric connector unit 23 electrically connected to the receiver 22 are incorporated in a housing 21 formed of a nonmagnetic material. The electric connector unit 23 is connected to the electric cable 12 connected to the CCU 6. The fixing unit 15 transmits power supply from the CCU 6 and a signal from the receiver 22 to the CCU 6 via the electric cable 12.

A slide hole 24 is formed in the housing 21 in a lateral direction from a side thereof. A tube fixing lever 26 composing a fixing section, on an end face of which an urging spring 25 is fixed and which is formed of a nonmagnetic material, is inserted through and arranged in the slide hole 24. The tube fixing lever 26 is a lever for nipping and fixing the tube member 41 (see FIGS. 4 to 6) of the camera 4 explained later. The fixing lever 26 is formed in a substantially rectangular parallelepiped shape and disposed slidably along the slide hole 24 in an inner direction of the housing 21. A hole 27 having a convex arcuate surface 27a on the urging spring 25 side is formed halfway in the tube fixing lever 26.

A tube inserting-through section 28 for the tube member 41 (see FIGS. 4 to 6) of the camera 4 to vertically pierce through the housing 21 is formed in the housing 21. In the tube inserting-through section 28, a conical taper surface 29 is formed to expand to an upper part serving as an opening in an upper surface of the housing 21.

In the fixing unit 15 configured as explained above, the hook needle 16 is inserted through and arranged in a hole, which pierces through the fixing unit 15 in the vertical direction, to be freely inserted and pulled in a slide position where the tube fixing lever 26 is pushed in the housing 21 such that the hole 27 of the tube fixing lever 26 and the tube inserting-through section 28 coincide with each other.

The hook needle 16 of the external device 3 includes a cylindrical puncture needle tube 31, a needle head 32 connected to an upper part of the puncture needle tube 31, a puncture rod 33 having a hook section 34, which is slidably inserted through the puncture needle tube 31, formed at a distal end portion thereof, a hook head 35 connected to an upper part of the puncture rod 33, and a spring 36 interposed between the hook head 35 and the needle head 32.

The puncture needle tube 31 is an elongated metal pipe of about 3 mm in diameter formed in a sharp needle shape obliquely cut at a distal end portion thereof. The needle head 32 has an outer diameter larger than that of the puncture needle tube 31 and is formed in a conical shape on a distal end side and integrally formed with the puncture needle tube 31. The needle head 32 comes into contact with a taper surface 29 formed in an upper part of the housing 21 to prevent the hook needle 16 from coming off downward in the housing 21.

The puncture rod 33 is an elongated metal bar. In the puncture rod 33, the hook head 35 connected to the upper part thereof is urged in a direction away from the needle head 32 by the spring 36. Consequently, in the puncture rod 33, the hook section 34 formed at the distal end portion is housed in the puncture needle tube 31.

In the hook needle 16, when the hook head 35 is pushed into the puncture needle tube 31 by a surgeon against the urging force of the spring 36 (as indicated by an arrow F in FIG. 3), the hook section 34 formed at the distal end portion projects from the distal end portion of the puncture needle tube 31.

The tube fixing lever 26 is inserted through and fixed in the housing 21 by the pressing force in an outer side direction of the housing 21 caused by the urging force of the urging spring 25 in a state in which the hook needle 16 configured in this way is inserted through and arranged in the tube inserting-through section 28 of the housing 21 and the hole 27 of the tube fixing lever 26. In other words, an outer circumferential surface of the puncture needle tube 31 is pressed by the arcuate surface 27a formed on one side of the hole 27 of the tube fixing lever 26 and comes into contact with an inner surface of the tube inserting-through section 28, whereby the hook needle 16 is fixed in a state inserted through the housing 21.

The camera 4 is explained in detail with reference to FIGS. 4 to 6.

As shown in FIG. 4, the camera 4 mainly includes a camera unit 47 as image pickup means composing an image pickup section, and a camera holding section 48 as holding means composing a holding section, which that holds the camera unit 47, coupled to the camera unit 47 via two arm sections 49 as coupling means composing a coupling section.

The camera unit 47 includes a substantially columnar camera housing 51 and a dome-like transparent cover member 52 hermetically fixed to one side, i.e., a front surface of the camera housing 51.

As shown in FIG. 5, an image pickup unit 50, small and low power-consumption plural, i.e., two illumination units 57 composed of LEDs, organic ELDs, or the like as light sources of illumination light, a transmitter 58 for transmitting an image pickup signal from the image pickup unit 50 to the outside by radio, and a battery 59 composing a power supply unit for feeding power to the image pickup unit 50 and the illumination units 57 are incorporated in the camera housing 51. An image signal photoelectrically converted by the image pickup unit 50 is transmitted from the transmitter 58 to the receiver 22 disposed in the housing 21 of the external device 3.

The image pickup unit 50 mainly includes a solid-state image pickup device 55 such as a CCD or a CMOS that photoelectrically converts photographing light made incident thereon and an object lens group 56 that condenses the photographing light on the solid-state image pickup device 55. In the image pickup unit 50 of the camera unit 47 according to the present embodiment, an image pickup optical system that picks up images in a wide-angle field of view range is set such that a photographable angle of view β (see FIG. 16) thereof is, for example, equal to or larger than 90°.

The camera holding section 48 is formed in a spherical shape at one end and has a so-called cannonball shape as an external shape such that the camera unit 47 that pivotally moves as explained later does not come into contact with the vicinities of both the ends of the two arm sections 49 provided in both ends of the camera holding section 48. An operation grasping section 61 explained later is provided to project from the other end of the camera holding section 48. A suction cup 42 formed of a flexible elastic member such as silicon rubber is fit and fixed to an upper side of the camera holding section 48.

A through hole is formed in the center of the suction cup 42. One end of a tube member 41 for lifting having a predetermined length is locked to the through hole.

The flexible suction cup 42 configures abdominal wall fixing means as an abdominal wall fixing section that, when the tube member 41 is pulled with tension equal to or larger than fixed tension, adheres to a body inner wall (an abdominal cavity wall) as explained later while the end thereof expanding and deforming and fixes the camera unit 47 in the body inner wall together with the camera holding section 48. The suction cup 42 is detachably attachable to the camera holding section 48 such that the suction cup 42 can be replaced when deteriorated.

An operation wire 45 is inserted through and arranged in the tube member 41. The operation wire 45 is inserted through and arranged in one arm section 49 via a holding-section-side wire inserting-through hole 43 formed in the camera holding section 48. The operation wire 45 is provided to be folded in one end of the arm section 49, through which the operation wire 45 is inserted and arranged, such that both ends thereof extend out from the tube member 41. In other words, both end sides of one folded operation wire 45 extend out from the tube member 41. The operation wire 45 may be a thread such as a surgical suture or may be a twisted yarn made of metal.

In the present embodiment, the operation grasping section 61 includes a grasping member 61a having a ring shape as a shape of one end and a shaft 61b coupled to the grasping member 61a. The shaft 61b is pivotably inserted through and arranged in a hole 44 formed in the camera holding section 48. A bevel gear 63 is provided at the other end of the shaft 61b arranged in the operation grasping section 61. The bevel gear 63 is arranged in a space section 40 formed to communicate with the hole 44 of the camera holding section 48 through which the shaft 61b is inserted.

In the operation grasping section 61, the shaft 61b is pivotally supported by a bearing 64 provided in an opening portion where the hole 44 communicates with the space section 40 of the camera holding section 48. An O ring 65 for maintaining watertightness with respect to the pivoting shaft 61b is provided in an opening portion of the hole 44 of the camera holding section 48 through which the grasping member 61a of the operation grasping section 61 extends out.

The bevel gear 63 of the operation grasping section 61 is provided halfway in an arm pivoting shaft 81 orthogonal to the shaft 61b and meshes with a bevel gear 82 arranged in the space section 40 of the camera holding section 48. The arm pivoting shaft 81 is pivotably provided to pierce through the camera holding section 48. Both ends of the arm pivoting shaft 81 are locked to the arm sections 49. The arm pivoting shaft 81 is pivotally supported by two bearings 83 provided in the camera holding section 48.

In the arm pivoting shaft 81, rubber rings 85 for watertightness maintenance are provided between the camera holding section 48 and the arm sections 49. A ring member 86 for reinforcement through which the arm pivoting shaft 81 is inserted is provided in an outer circumferential portion of the camera holding section 48.

The arm pivoting shaft 81 is coupled to two click mechanism units 84 composing a pivoting position fixing mechanism provided in opposed two wall portions in the space section 40 of the camera holding section 48 through which the arm pivoting shaft 81 pierces. As shown in FIG. 7, each of the two click mechanism units 84 includes an annular member 87 and a disc member 88 fixed to the arm pivoting shaft 81.

Plural protrusions 88a provided at equal intervals are formed in an outer circumferential portion of the disc member 88. A protrusion 87a that comes into contact with one of the plural protrusions 88a of the disc member 88 during pivoting of the arm pivoting shaft 81 is formed on an inner circumferential surface of the annular member 87.

In the click mechanism unit 84 configured in this way, the disc member 88 fixed to the arm pivoting shaft 81 is arranged in the annular member 87. The protrusion 87a formed on the inner circumferential surface of the annular member 87 and one of the plural protrusions 88a formed on the outer circumference of the disc member 88 fixed to the arm pivoting shaft 81 come into contact with each other. Consequently, the arm pivoting shaft 81 can be stepwise fixed in pivoting positions desired by the surgeon. A protrusion amount of the protrusions 87a and 88a are set such that the plural protrusions 88a formed in the outer circumference of the disc member 88 can climb over the protrusion 87a formed on the inner circumferential surface of the annular member 87 with predetermined pivoting force.

Referring back to FIG. 6, the two arm sections 49 are fixed in one end portions of the arm sections 49, respectively, such that the arm pivoting shaft 81 is orthogonal to a longitudinal direction. Cap members 71 covering connecting portions of the arm pivoting shaft 81 are provided in one end portions of the two arm sections 49.

When the operation grasping section 61 serving as one of operation means as an operation section for pivotally operating the camera unit 47 pivots, the bevel gear 63 of the operation grasping section 61 transmits pivoting force to the bevel gear 82 of the arm pivoting shaft 81 with which the bevel gear 63 meshes. The two arm sections 49 are pivoted around the arm pivoting shaft 81. When the operation grasping section 61 is pivoted around an A axis shown in FIG. 6, the arm pivoting shaft 81 pivots around a B axis orthogonal to the A axis according to the transmission of the pivoting force by the bevel gears 63 and 82. Therefore, the two arm sections 49 fixed to both ends of the arm pivoting shaft 81 pivot around the A axis.

The operation wire 45 is inserted through and arranged in one arm section 49 of the two arm sections 49. The operation wire 45 is arranged from the holding-section-side wire inserting-through hole 43 formed in the camera holding section 48 to an arm-side wire inserting-through hole 72 formed inside one arm section 49.

A hollow section 73 that communicates with the arm-side wire inserting-through hole 72 is formed in an end of one arm section 49 coupled to the camera unit 47. In the hollow section 73, a pulley 74 provided in a camera pivoting shaft 75 fixed to the camera housing 51 of the camera unit 47 is arranged. The camera pivoting shaft 75 is pivotably coupled to the two arm sections 49. Cap members 76 covering connecting portions of the camera pivoting shaft 75 are also provided at the other ends of the two arm sections 49. The camera pivoting shaft 75 and the arm pivoting shaft 81 in the present embodiment are parallel shafts.

The operation wire 45 is disposed to be folded in the pulley 74. The operation wire 45 is hooked to an outer circumference of the pulley 74. When both the ends of the operation wire 45 are tugged and relaxed in opposite directions, the pulley 74 pivots.

Consequently, the camera pivoting shaft 75 to which the pulley 74 is fixed is pivoted relative to the two arm sections 49 according to the operation of the operation wire 45 serving as one of the operation means as the operation section that pivots the camera unit 47. When the camera pivoting shaft 75 pivots in this way, the camera unit 47 fixed to the camera pivoting shaft 75 is also pivoted around the B axis shown in FIG. 6 relative to the two arm sections 49. The click mechanism units explained above may be provided in the camera pivoting shaft 75 such that the camera unit 47 can be stepwise fixed in pivoting positions desired by the surgeon.

An annular member 77 for protection is provided in the opening portion of the arm-side wire inserting-through hole 72, which communicates with the hollow section 73, because the operation wire 45 rubs against the opening portion. Further, because of the same reason, annular members 78 and 79 are provided in the opening portions of the holding-section-side wire inserting-through hole 43 and the arm-side wire inserting-through hole 72.

The endoscope system 1 according to the present embodiment configured as explained above is used for the laparoscopic surgical operation and used for treatment inside the abdominal cavity that is one of body cavities of a patient.

A procedure for setting the endoscope system 1 according to the present embodiment in the abdominal cavity as the body cavity of the patient for the laparoscopic surgical operation and an action of the endoscope system 1 are explained in detail below with reference to FIGS. 8 to 16.

First, the surgeon cuts small dissected portions in two places of an abdominal wall 102 of a patient 100 using a knife or the like. As shown in FIG. 8, the surgeon penetrates trocars 110 and 111 in the dissected portions. The surgeon dissects the abdominal wall 102 in another place (position) a predetermined distance away from the trocar 110 for leading the rigid endoscope 2 into an abdominal cavity 101 and penetrates, into the abdominal cavity 101, the trocar 111 for leading a treatment instrument 120 such as grasping forceps into the abdominal cavity 101.

As shown in FIGS. 2 and 3, the surgeon inserts the puncture needle tube 31 of the hook needle 16 into the tube inserting-through section 28 provided in the fixing unit 15 of the external device 3. In inserting the puncture needle tube 31, the surgeon pushes the tube fixing lever 26 into the housing 21 such that the puncture needle tube 31 pierces through the fixing unit 15. The surgeon inserts the puncture needle tube 31 such that the puncture needle tube 31 pierces through the hole 27 of the tube fixing lever 26.

The surgeon locates the fixing unit 15 sufficiently on the needle head 32 side on the top side of the puncture needle tube 31 and sufficiently projects the puncture needle tube 31 from the bottom surface of the fixing unit 15 (see FIGS. 2 and 3). In this state, the fixing unit 15 does not come off from the puncture needle tube 31 because the arcuate surface 27a as one wall surface of the hole 27 of the tube fixing lever 26 comes into contact with and holds the puncture needle tube 31 with the urging force of the urging spring 25.

Subsequently, the surgeon inserts the insertion portion 8 of the rigid endoscope 2 into the abdominal cavity 101 via the trocar 110 (see FIG. 9). The surgeon grasps, for example, the ring-like grasping member 61a of the operation grasping section 61 projecting from the camera holding section 48 with the treatment instrument 120 such as the grasping forceps via the other trocar 111 and inserts the camera 4 into the abdominal cavity 101. It is advisable that the surgeon inserts the camera 4 into the abdominal cavity 101 while checking an image formed by the rigid endoscope 2.

As shown in FIGS. 9 and 10, the surgeon penetrates the puncture needle tube 31 of the hook needle 16 inserted and held in the fixing unit 15, which composes the external device 3, while checking an image formed by the rigid endoscope 2 such that the puncture needle tube 31 pierces through the abdominal wall 102. As shown in FIG. 10, the surgeon pushes the hook head 35 in a direction indicated by an arrow F in the figure in order to lead out the puncture rod 33 from the puncture needle tube 31. From this state, the surgeon hooks the hook section 34 formed in the puncture rod 33 on the tube member 41 of the camera 4 while looking at an image formed by the rigid endoscope 2.

When the tube member 41 is hooked on the hook section 34, the surgeon releases the push-in of the hook head 35 of the puncture rod 33. Then, the puncture rod 33 is led into the puncture needle tube 31 in a state in which the tube member 41 is hooked on the hook section 34.

Thereafter, as shown in FIG. 12, the surgeon pulls the puncture needle tube 31 of the hook needle 16 from the abdominal cavity 101 to the outside of the body (in an UP direction in the figure) in a state in which the tube member 41 is hooked on the hook section 34 of the puncture rod 33. As shown in FIG. 13, the surgeon pulls the puncture needle tube 31 of the hook needle 16 from the abdominal cavity 101, moves the fixing unit 15 in an abdomen direction of the patient 100 (a DOWN direction in the figure) relatively to the puncture needle tube 31, and tugs the puncture needle tube 31 until the tube member 41 is pierced through the tube inserting-through section 28 of the fixing unit 15.

When the surgeon tugs the puncture needle tube 31, the surgeon can easily slide the fixing unit 15 relatively to the puncture needle tube 31 of the hook needle 16 by pushing the tube fixing lever 26 of the fixing unit 15 to an inner side of the housing 21 (an arrow P direction in FIG. 13). When the tube member 41 is pierced through the tube inserting-through section 28 of the fixing unit 15, as shown in FIG. 13, the surgeon moves the fixing unit 15 relatively to the tube member 41 in the abdomen direction (the DOWN direction in the figure) of the patient 100 while tugging the tube member 41 (in the UP direction in the figure).

In other words, the surgeon can easily slide the fixing unit 15 relatively to the puncture needle tube 31 of the hook needle 16 and the tube member 41 of the camera 4 by maintaining a state in which the tube fixing lever 26 of the fixing unit 15 is pushed into the inner side of the housing 21.

The surgeon tugs the tube member 41 of the camera 4 until the fixing unit 15 and the camera 4 hold the abdominal wall 102 in a state in which the fixing unit 15 is placed on the abdomen of the patient 100 as shown in FIG. 14. When the surgeon confirms from an image formed by the rigid endoscope 2 that, as shown in FIG. 15, the suction cup 42 of the camera 4 comes into contact with the inner surface of the abdominal wall 102, the surgeon releases the push-in of the tube fixing lever 26 of the fixing unit 15.

Then, the tube fixing lever 26 of the fixing unit 15 receives the urging force of the urging spring 25 and moves in an arrow R direction shown in FIG. 15. The hole 27 shifts from the tube inserting-through section 28 of the housing 21. The tube member 41 inserted through the hole 27 and the tube inserting-through section 28 is nipped and fixed to the housing 21. Tension equal to or larger than fixed strength is always applied to the tube member 41 between the tube fixing lever 26 and the suction cup 42 because of deformation of the elastic suction cup 42. Consequently, the tension equal to or larger than the fixed strength applied to the tube member 41 is always maintained and the fixing unit 15 and the camera 4 are maintained and fixed in a state in which the fixing unit 15 and the camera 4 hold the abdominal wall 102.

In this way, as shown in FIG. 16, the camera 4 is set in the abdominal cavity 101 of the patient 100 in a surely stable state. The laparoscopic surgical operation is performed by the endoscope system 1 according to the present embodiment. For example, one end of a not-shown pneumoperitoneum tube is attached to the trocar 110 and, for example, a carbon dioxide gas is injected into the abdominal cavity 101 as gas for pneumoperitoneum for the purpose of securing a field of vision of the rigid endoscope 2 and for the purpose of securing an area for operating a surgical instrument and the like. The surgeon inserts the rigid endoscope 2 into the trocar 110 and inserts the treatment instrument 120 into the trocar 111 to perform the laparoscopic surgical operation in a state in which the camera 4 is placed in the abdominal cavity 101 to be caused to adhere to the abdominal wall 102.

During the manipulation of the laparoscopic surgical operation, when the surgeon rotates the grasping member 61a of the operation grasping section 61, which projects from the camera holding section 48 of the camera 4, around an A axis (in a direction along an arrow "a") shown in FIG. 17 using the treatment instrument 120 such as the grasping forceps, the surgeon can pivotally move camera unit 47 around a B axis (in a direction along an arc-like arrow "b") in the figure on the one end sides of the two arm sections 49 coupled to the camera holding section 48. Consequently, the surgeon can move the camera unit 47 to a desired position in a swinging range of the two arm sections 49 relative to the camera holding section 48 and change a photographing range.

The operator can pivotally move the camera unit 47 around a C axis (in a direction along an arc-like arrow "c") in the figure on the other end sides of the arm sections 49 by alternately tugging and relaxing the operation wire 45 extending out from the tube member 41 on the outside of the body as shown in FIG. 18. Consequently, the surgeon can change an image pickup visual field direction of the camera unit 47 to a desired direction.

When the surgeon finishes the laparoscopic surgical operation, the surgeon pulls the fixing unit 15 from the tube member 41 while pushing the tube fixing lever 26 of the fixing unit 15 to the inner side of the housing 21. The surgeon grasps the camera 4 in the abdominal cavity 101 with the treatment instrument 120 such as the grasping forceps and takes out the camera 4 outside from the abdominal cavity 101 via the trocar 111.

With the endoscope system 1 according to the present embodiment explained above, it is possible to observe the body tissue inside the body cavity, i.e., the abdominal cavity 101 in multiple viewpoints including a wide angle. For example, an entire excision line in a surgery of a large organ or excision of the large intestine can be easily grasped. With the endoscope system 1, when the small camera 4 led into the abdominal cavity 101 separately from the rigid endoscope 2 for enlarged observation is set, it is possible to perform a low-invasive surgery without increasing burden on a patient. As a result, treatment by the laparoscopic surgical operation is facilitated by using the endoscope system 1 according to the present invention.

The camera 4 can move the camera unit 47 as the image pickup means composing the image pickup section to a desired position in a swinging range of the two arm sections 49 and change a photographing range, and can change an image pickup visual field direction of the camera unit 47 to a desired direction in a limited space in the body. In other words, the camera 4 can freely change, with pivoting operation of the arm sections 49 relative to the camera holding section 48 placed and fixed on the abdominal wall 102 by the suction cup 42 as the abdominal wall fixing section, a distance between the camera unit 47 and the subject within the swinging range of the arm sections 49 and change a photographing range and a photographing direction of the camera unit 47 relative to the subject.

As explained above, the camera 4 as the medical apparatus according to the present embodiment can change a distance between the camera unit 47 as the image pickup means composing the image pickup section and the subject in a state in which the camera 4 is fixed to the abdominal wall 102. Therefore, the camera 4 can perform magnified observation by moving the camera unit 47 to be closer to the subject without using a zoom function. Further, the camera 4 can photograph the subject from different angles by changing a photographing direction.

(First Modification)

A first modification of the camera 4 explained above is explained below with reference to FIG. 19.

As shown in FIG. 19, in the camera 4 according to this modification, the camera holding section 48 is slidable relative to a cylinder 48a to which the suction cup 42 as the abdominal wall fixing section is fixed. A trunk section 48b inserted through the cylinder 48a with predetermined frictional force is provided in the camera holding section 48.

The camera holding section 48 configured as explained above is slidable in a front to back direction along an arrow "d" in the figure in a range of a longitudinal direction of the trunk section 48b relative to the cylinder 48a placed and fixed on the abdominal wall 102 by the suction cup 42. The camera holding section 48 is also pivotable in a direction along an arc-like arrow "e" in the figure around the longitudinal direction of the trunk section 48b. In the trunk section 48b, an outward flange section 48c for preventing the trunk section 48b from coming off from the cylinder 48a is provided at one end where the grasping member 61a of the operation grasping section 61 extends out.

As explained above, the camera 4 can move the camera unit 47 in the front to back direction along the arrow "d" in the figure in the range in the longitudinal direction of the trunk section 48b and the direction along the arc-like arrow "e" around the longitudinal direction of the trunk section 48b in addition to the pivotal movement around the B axis (in the direction along the arc-like arrow "b") in the figure of the two arm sections 49 by the operation around the A axis (in the direction along the arrow "a") of the grasping member 61a of the operation grasping section 61 and the pivotal movement around the C axis (in the direction along arc-like the arrow "c") by the alternate tugging and relaxing of the operation wire 45.

The trunk section 48b is slid and pivoted relative to the cylinder 48a by the treatment instrument 120 such as the grasping forceps. A position to which the trunk section 48b is slid and a posture of the trunk section 48b after pivoting are maintained by predetermined frictional force with the cylinder 48a.

In addition to the effects explained above, the camera 4 as the medical apparatus according to this modification configured as explained above can variously change a photographing position, a photographing direction (angle), and a photographing distance of the camera unit 47 relative to the subject.

(Second Modification)

A second modification of the camera 4 is explained with reference to FIG. 20.

In the camera 4 according to this modification, a telescopic pole 90 as a plural-stage telescopic unit is provided in the center at a rear end on the opposite side of a photographing direction of the camera unit 47. A distance between the camera unit 47 and the camera holding section 48 can be changed.

Each of plural annular members slides, whereby the telescopic pole 90 extends and contracts. When the telescopic pole 90 contracts, the annular members are housed. The telescopic pole 90 has a configuration in which the arm sections 49 are coupled to the arm connecting section 91 provided on the opposite side of the camera unit 47.

The camera 4 configured as explained above can change the distance between the camera unit 47 and the camera holding section 48 when the surgeon grasps the camera unit 47 itself with the treatment instrument 120 such as the grasping forceps and extends and contracts the telescopic pole 90 in the arrow "f" direction in the figure.

In addition to the effects explained above, the camera 4 configured as explained above as the medical apparatus according to this modification can swing and move the camera unit 47 by changing an extension and contraction amount of the telescopic pole 90 in addition to the length of the arm sections 49 such that the camera 4 can photograph the subject in a position close to the subject.

The invention described in the embodiment is not limited to the embodiment and the modifications. Besides, at an implementation stage, various modifications can be carried out without departing from the spirit of the invention. Inventions at various stages are included in the embodiments. Various inventions can be extracted according to appropriate combinations in plural elements disclosed herein.

For example, when the problems to be solved by the invention can be solved and the effects of the invention can be obtained even if several elements are deleted from all the elements described in the embodiment, a configuration in which the elements are deleted can be extracted as an invention.

What is claimed is:

1. A medical apparatus used in a state in which the medical apparatus is led into a body and fixed, the medical apparatus comprising:
    an image pickup section that picks up an image of a subject in the body and is provided pivotably around a first axis;
    a holding section that holds the image pickup section pivotably around a second axis different from the first axis;
    a coupling section that couples the image pickup section with the holding section, holds the image pickup section pivotably around the first axis, and holds the image pickup section pivotably around the second axis with respect to the holding section;
    a fixing section that is connected with a tube member that is inserted and fixed in an external device set on a surface of the body, the fixing section placing and fixing the holding section on a body wall in the body;
    an operation wire that is inserted and arranged in the tube member, the operation wire operating the image pickup section pivotally held to the coupling section around the first axis from outside the body; and
    an operation grasping section that is disposed to the holding section and grasped when the medical apparatus is led into the body, the operation grasping section being operated to cause the coupling section to pivot around the second axis from inside the body.

2. The medical apparatus according to claim 1, further comprising a fixing mechanism for fixing stepwise the image pickup section, which is pivoted around the first axis and around the second axis, in predetermined pivoting positions.

3. The medical apparatus according to claim 1, wherein the holding section includes a trunk section that slidably and pivotably relative to a cylinder to which the fixing section is fixed.

4. The medical apparatus according to claim 3, further comprising a coupling section that couples the image pickup section and the holding section, holds the image pickup section pivotably around the first axis, and holds the holding section pivotably around the second axis.

5. The medical apparatus according to claim 3, further comprising:
    a first operation section for pivoting the image pickup section around the first axis; and
    a second operation section for pivoting the image pickup section around the second axis.

6. The medical apparatus according to claim 3, further comprising a fixing mechanism for fixing stepwise the image pickup section, which is pivoted around the first axis and around the second axis, in predetermined pivoting positions.

7. The medical apparatus according to claim 1, wherein the coupling section includes a telescopic unit that changes a distance between the image pickup section and the holding section.

* * * * *